(12) United States Patent
Soon-Shiong et al.

(10) Patent No.: US 10,973,852 B2
(45) Date of Patent: Apr. 13, 2021

(54) NK CELLS WITH ALTERED CXCL12/CXCR4 SIGNALING

(71) Applicant: Nant Holdings IP, LLC, Culver City, CA (US)

(72) Inventors: Patrick Soon-Shiong, Culver City, CA (US); Shahrooz Rabizadeh, Culver City, CA (US); Kayvan Niazi, Culver City, CA (US)

(73) Assignee: NantCell, Inc., Culver City, CA (US)

( * ) Notice: Subject to any disclaimer, the term of this patent is extended or adjusted under 35 U.S.C. 154(b) by 280 days.

(21) Appl. No.: 16/071,860

(22) PCT Filed: Jan. 25, 2017

(86) PCT No.: PCT/US2017/014840
§ 371 (c)(1),
(2) Date: Jul. 20, 2018

(87) PCT Pub. No.: WO2017/132202
PCT Pub. Date: Aug. 3, 2017

(65) Prior Publication Data
US 2019/0083533 A1 Mar. 21, 2019

Related U.S. Application Data

(60) Provisional application No. 62/286,909, filed on Jan. 25, 2016.

(51) Int. Cl.

| | | |
|---|---|---|
| *A61K 48/00* | (2006.01) | |
| *C07H 21/02* | (2006.01) | |
| *C07H 21/04* | (2006.01) | |
| *A61K 35/17* | (2015.01) | |
| *A61K 38/17* | (2006.01) | |
| *A61K 38/19* | (2006.01) | |
| *C07K 14/52* | (2006.01) | |
| *C07K 14/715* | (2006.01) | |
| *C12N 5/0783* | (2010.01) | |
| *A61K 45/06* | (2006.01) | |
| *A61P 35/00* | (2006.01) | |

(52) U.S. Cl.
CPC .......... *A61K 35/17* (2013.01); *A61K 38/1793* (2013.01); *A61K 38/195* (2013.01); *A61K 45/06* (2013.01); *A61P 35/00* (2018.01); *C07K 14/521* (2013.01); *C07K 14/7158* (2013.01); *C12N 5/0646* (2013.01); *C07H 21/02* (2013.01); *C07H 21/04* (2013.01); *C12N 2510/00* (2013.01)

(58) Field of Classification Search
CPC .. C12N 15/85; C12N 2510/00; C12N 5/0646; C07H 21/02; C07H 21/04
USPC .............. 424/93.21; 536/23.1, 23.5
See application file for complete search history.

(56) References Cited

U.S. PATENT DOCUMENTS

| 8,557,964 B2 | 10/2013 | Klinguer-Hamour et al. |
| 8,748,107 B2 | 6/2014 | Kavlie et al. |
| 2006/0292156 A1 | 12/2006 | Campbell |
| 2016/0184234 A1 | 6/2016 | Poznansky et al. |

FOREIGN PATENT DOCUMENTS

| WO | 2010107493 | 9/2010 |
| WO | 2016011381 | 1/2016 |
| WO | 2016102660 | 6/2016 |

OTHER PUBLICATIONS

Nakamura et al. "Fratricide of natural killer cells dressed with tumor-derived NKG2D ligand", PNAS, Jun. 4, 2013, vol. 110, No. 23, pp. 9421-9426.
Mueller et al. "Engineering NK cells modified with an EGFRvIII-specific chimeric antigen receptor to overexpress CXCR4 improves immunotherapy of CXCL12/SDF-1α-secreting glioblastoma" HHS Public Access, Jun. 1, 2016.
Teicher et al. "CXCL12 (SDF-1)/CXCR4 Pathway in Cancer" American Association for Cancer Research, Jan. 8, 2016, pp. 2927-2931.
Noda et al. "CXCL12-CXCR4 chemokine signaling is essential for NK-cell development in adult mice" Blood, Jan. 13, 2011, vol. 117, No. 2.
Taniguchi et al. "2B4 inhibits NK-cell fratricide", University of Chicago Department of Pathology, Blood, Sep. 15, 2007, vol. 110, No. 6.
Busillo et al. "Regulation of CXCR4 Signaling", NIH Public Access, Apr. 1, 2008.
Nakamura et al. "NK-cell fratricide: Dynamic crosstalk between NK and cancer cells", ISSN: (Print) 2162-402X (Online) Journal homepage: http://www.tandfonline.com/loi/koni20, Oct. 10, 2013.
Biagi et al. "Chimeric T-cell receptors: new challenges for targeted immunotherapy in hematologic malignancies" haematologica/the hematology journal, 2007, pp. 381-388.
Carlsten et al., "Genetic manipulation of NK cells for cancer immunotherapy: techniques and clinical implications", Frontiers in Immunology, vol. 6, Article 266, Jun. 10, 2015, pp. 9.

(Continued)

*Primary Examiner* — Shin Lin Chen
(74) *Attorney, Agent, or Firm* — Martin Fessenmaier; Umberg Zipser LLP

(57) ABSTRACT

NK cell based cancer immunotherapy, and particularly genetically modified NK92 cell-based immunotherapy is enhanced by expression CXCL12 and/or by suppression or deletion of CXCR4 in the natural killer cells to so reduce aggregation, rejection, and/or fratricide of the natural killer cells. Provided herein are genetically engineered NK (natural killer) cell comprising a recombinant nucleic acid encoding at least a portion of chemokine C—X—C motif ligand 12 (CXCL12), and a transcript for downregulation of chemokine C—X—C motif receptor 4 (CXCR4).

15 Claims, No Drawings

(56) References Cited

OTHER PUBLICATIONS

Domanska et al., "A review on CXCR4/CXCL12 axis in oncology: No place to hide", European Journal of Cancer, vol. 49, No. 1, Jan. 1, 2013, pp. 219-230.
Yang et al., "NK cell-based cancer immunotherapy: from basic biology to clinical application" Science China Life Sciences, vol. 58, No. 12, Nov. 20, 2015, pp. 13.
Ames et al., "Advantages and clinical applications of natural killer cells in cancer immunotherapy", Cancer Immunology, Immunotherapy, vol. 63, No. 1, Aug. 30, 2013, pp. 8.
Extended European Search Report received for EP Application No. 17744803.2, dated Aug. 6, 2019, pp. 6.

NK CELLS WITH ALTERED CXCL12/CXCR4 SIGNALING

This application claims priority to US provisional application with the Ser. No. 62/286,909, filed Jan. 25, 2016.

FIELD OF THE INVENTION

The field of the invention is recombinant cells, and compositions and methods of use of such recombinant cells, particularly as it relates to natural killer cells (NK cells) that are engineered to express recombinant CXCL12 and/or not to express CXCR4.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications are incorporated by reference herein to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

More recently, activated NK cells have become available as potential cell therapeutic agents. Advantageously, such cells can be further modified to impart target specificity (e.g., URL: www.NantKwest.com) for cell-specific cancer therapy. While such modified cells hold great promise for immunotherapy of cancer, activated NK cells tend to exhibit fratricide (possibly via an NKG2D mediated cascade of events as described in *Proc Natl Acad Sci* USA 2013). In addition, activated NK cells may also aggregate and become therapeutically less effective. Moreover, NK allografts are often prone to recognition by the host immune system and may therefore be eliminated before a desired therapeutic effect can be achieved.

It was previously reported that 2B4-CD48 interactions among NK cells are required for optimal NK functions, and indeed, that in the absence of proper 2B4-CD48 interactions, activated NK cells will undergo perform-dependent fratricide. However, due to the criticality of the 2B4-CD48 interaction, interference with that signaling pathway is not considered a suitable option for reduction of NK fratricide (see e.g., *Blood* 2007; 110: 2020-2023).

CXCL12-CXCR4 chemokine signaling is essential for numerous physiological and developmental processes in NK cells. For example, NK cell development has been shown to require CXCR4 signaling (see e.g., *Blood* 2011; 117: 451-458). In addition, resting NK cells exhibit strong migration in response to CXCL12 (see e.g., *J Leukoc Biol* 2002; 71: 173-183). Moreover, CXCL12-CXCR4 chemokine signaling has also been shown to be involved in various tumor signaling pathways (see e.g., *Clin Cancer Res* 2010;16: 2927-2931). However, there are diverse NK cell populations (e.g., $CD56^{(dim)}$ $CD16^+$ and $CD56^{(bright)}$ $CD16^-$), and different subgroups exhibit often quite different responses to CXCL12-CXCR4 chemokine signaling. For at least this reason, interference with CXCL12-CXCR4 chemokine signaling in native NK cells is generally not considered a therapeutic strategy for NK cell-based therapy.

Thus, while numerous aspects of NK cells are well known in the art, there is still a need for improved treatment systems and methods that use NK cells in immunotherapy of various cancers, and especially where the NK cells are NK92 derivatives.

SUMMARY OF THE INVENTION

The inventors have discovered that cancer immunotherapy can be augmented/effected using genetically engineered NK cells, and especially NK92 cells, that overexpress CXCL12 and/or do not express CXCR4 or are treated with a CXCR4 inhibitor. While in most cases allogenic with respect to a recipient, genetically engineered cells presented herein are thought to be less likely targeted by host immune cells and less likely to commit fratricide.

Therefore, in one aspect of the inventive subject matter, the inventors contemplate a genetically engineered NK (natural killer) cell that comprises a recombinant nucleic acid encoding at least a portion of CXCL12 and/or a transcript for downregulation of CXCR4. Additionally, or alternatively, such NK cell may also be modified to have a deletion or knockout mutation for CXCR4, or may be treated with an CXCR4 inhibitor.

Preferred NK cells will be immortalized, and most preferably be genetically engineered NK92 cells. For example, the natural killer cell is genetically engineered to have a reduced or abolished expression of at least one killer cell immunoglobulin-like receptor (KIR, typically a KIR having two domains). Where desired, the natural killer cell may also be genetically engineered to express a high-affinity Fcγ receptor (and most typically a FcγIII receptor) to which an antibody may be coupled. Suitable antibodies will have binding specificity against a tumor associated antigen, a tumor specific antigen, or a cancer neoepitope. In yet further examples, the natural killer cell may also be genetically engineered to express a chimeric T-cell receptor, preferably having an scFv portion, and/or wherein the chimeric T-cell receptor has an ectodomain with binding specificity against a tumor associated antigen, a tumor specific antigen, and a cancer neoepitope.

In further contemplated aspects, the at least portion of the CXCL12 is a full length variant of CXCL12, or a truncated agonist variant of CXCL12 that binds to CXCR4. Moreover, the transcript for downregulation of CXCR4 may be an shRNA or a siRNA, or the cell may have a deletion or knockout mutation for CXCR4. Alternatively, CSXR4 may also be inhibited using a small molecule or antibody (or fragment thereof).

Therefore, in a further aspect of the inventive subject matter, the inventors also contemplate a method of preparing a pharmaceutical composition that includes a modified genetically engineered NK cell. Such methods will typically include a step of introducing into a (typically genetically engineered) NK cell a recombinant nucleic acid that encodes at least a portion of CXCL12 and/or a transcript for downregulation of CXCR4, and/or a step of genetically modifying the genetically engineered NK cell to have a deletion or knockout mutation for CXCR4. In a further step, the modified NK cell is propagated in a first medium to a desired quantity, and in a still further step, the first medium is replaced with a second medium suitable for injection of the modified genetically engineered NK cells.

As noted above, the NK cell is preferably immortalized or a genetically engineered NK92 cell. For example, the NK cell may be genetically engineered to have a reduced or abolished expression of at least one killer cell immunoglobulin-like receptor (KIR), or may be genetically engineered to express a high-affinity Fcγ receptor, or may be genetically engineered to express a chimeric T-cell receptor. Likewise, the at least portion of the CXCL12 is a full length variant of CXCL12 or a truncated agonist variant of CXCL12 that binds to CXCR4, and/or the recombinant nucleic acid further encodes a transcript for downregulation of CXCR4, or the NK cell is modified to have the deletion or knockout mutation for CXCR4.

Consequently, the inventors also contemplate pharmaceutical compositions comprising a genetically engineered natural killer cell according to the inventive subject matter. Such compositions may further comprise an immune checkpoint inhibitor or other immune- or chemotherapeutic agent.

In still further contemplated aspects of the inventive subject matter, the inventors also contemplate a method of treating a patient that includes a step of administering a genetically engineered natural killer cell as described herein, wherein the administration is to a person in need thereof under a protocol effective to deliver the genetically engineered natural killer cell to a tumor in the patient. Where desired, treatment methods may further include a step of administering an immune checkpoint inhibitor or other immune- or chemotherapeutic agent to the patient.

Viewed from a different perspective, the inventors also contemplate use of a genetically engineered natural killer cell as described herein in the manufacture of a medicament to treat a tumor cell in a patient or to reduce tumor cell burden in a patient having a tumor. Suitable methods and uses will also include administration of the cells directly into the tumor (e.g., via injection). Co-administration with an immune checkpoint inhibitor is further contemplated where desired or otherwise indicated.

Various objects, features, aspects and advantages of the inventive subject matter will become more apparent from the following detailed description of preferred embodiments.

DETAILED DESCRIPTION

In view of the key role of CXCL12 in the chemoattraction and various other processes of NK cells (e.g., immune evasion from NK-mediated immune surveillance in neuroblastoma and multiple myeloma, NK cell homeostasis, etc.), the inventors discovered that interference with CXCL12-CXCR4 signaling in NK cells, and especially in NK92-based cells provided various therapeutic advantages, and especially reduced NK/NK cell fratricide and immune reaction of an allogenic host receiving NK cells, as well as reduced NK cell aggregation. Moreover, given the importance of CXCL12 in angiogenesis and tissue repair through recruitment of macrophages, the inventors also contemplate use of modified NK92 cells for indications outside of NK cell-based cancer treatment (e.g., autoimmunity, trauma, wound healing, etc). Consequently, the inventors contemplate genetic modification of NK cells, and especially NK92 cells and their derivatives, where such genetically modified cells (over)express CXCL12, a chemokine that represses interaction of cells expressing CXCL12 with those expressing CXCR4 such as T cells and other NK cells. Alternatively, or additionally, genetic modification also includes deletion of or suppression of expression of CXCR4, the receptor for CXCL12. Such genetic modification is deemed to reduce the likelihood of allografted NK92 cells and derivatives thereof from being targeted by host immune cells, and to reduce fratricide, and potentially reduce clumping of NK92 cells since the parental NK92 line also expresses CXCR4.

Most typically, (over)expression of CXCL12 will be achieved by introduction of a recombinant nucleic acid from which CXCL12 is expressed to so reduce adverse interaction between NK cells expressing CXCR4. Alternatively, or additionally, it is contemplated that NK cells may be modified to have reduced or no expression of CXCR4 using gene silencing (e.g., using RNA interference or antisense RNA), knockout or site-directed mutagenesis, or genome editing (e.g., using CRISPR-Cas9). By presentation of at least a portion of CXCL12 on the surface of the NK cells and/or removal of the CXCR4, it is believed that the thusly modified cells will be less subject to recognition and allograft rejection by the host and will have a reduced propensity to aggregate, while still retaining killing activity via NK cell-specific pathways.

With respect to suitable NK cells it is generally contemplated that the NK cells may be an autologous NK cell from a subject that will receive genetically modified NK cells. Such autologous NK cells may be isolated from whole blood, or cultivated from precursor or stem cells using methods well known in the art. Moreover, it should also be appreciated that the NK cells need not be autologous, but may be allogenic, or heterologous NK cells. However, in particularly preferred aspects of the inventive subject matter, the NK cells are genetically engineered to achieve one or more desirable traits, are NK92 cells or derivatives of NK92 cells. Additionally, suitable NK cells will also be continuously growing ('immortalized') cells. For example, in one particularly preferred aspect of the inventive subject matter, the genetically engineered NK cell is a NK92 derivative that is modified to have reduced or abolished expression of at least one killer cell immunoglobulin-like receptor (KIR), which will render such cells constitutively activated (via lack of or reduced inhibition).

NK92 cells exhibit an unusual receptor expression profile, expressing a relatively large number of activating (e.g., NKp30, NKp46, 2B4, NKGD, E, CD28) receptors. Conversely, NK92 cells also expresses few inhibitory receptors (e.g., NKGA/B, low levels of KIR2DL4, ILT-2), and lack most of the killer inhibitory receptors (KIRs) clonally expressed on normal NK cells. In addition, NK92 expresses relatively high levels of molecules involved in the perforin-granzyme cytolytic pathway as well as additional cytotoxic effector molecules including tumor necrosis factor (TNF)-superfamily members FasL, TRAIL, TWEAK, TNF-alpha, indicating the ability to kill via alternative mechanisms. Moreover, NK92 cells also express other molecules implicated immune effector cell regulation (CD80, CD86, CD40L, TRANCE) whose relevance in NK killing is unclear.

Moreover, suitable NK cells may have one or more modified KIR that are mutated such as to reduce or abolish interaction with MHC class I molecules. Of course, it should be noted that one or more KIRs may also be deleted or expression may be suppressed (e.g., via miRNA, siRNA, etc.). Most typically, more than one KIR will be mutated, deleted, or silenced, and especially contemplated KIR include those with two or three domains, with short or long cytoplasmic tail. Viewed from a different perspective, modified, silenced, or deleted KIRs will include KIR2DL1, KIR2DL2, KIR2DL3, KIR2DL4, KIR2DL5A, KIR2DL5B, KIR2DS1, KIR2DS2, KIR2DS3, KIR2DS4, KIR2DS5, KIR3DL1, KIR3DL2, KIR3DL3, and KIR3DS1. Such modified cells may be prepared using protocols well known in the art. Alternatively, such cells may also be commercially obtained from NantKwest (see URL www.nantkwest.com) as aNK cells ('activated natural killer cells). Such cells may then be additionally genetically modified to express CXCL12 or a portion thereof, and/or to have reduced or abolished expression of CXCR4 as further discussed below.

In another preferred aspect of the inventive subject matter, the genetically engineered NK cell may also be an NK92 derivative that is modified to express the high-affinity Fcγ receptor (CD16). Sequences for high-affinity variants of the Fcγ receptor are well known in the art (see e.g., *Blood* 2009 113:3716-3725), and all manners of generating and expression are deemed suitable for use herein. Expression of such receptor is believed to allow specific targeting of tumor cells using antibodies that are specific to a patient's tumor cells (e.g., neoepitopes), a particular tumor type (e.g., her2neu, PSA, PSMA, etc.), or that are associated with cancer (e.g., CEA-CAM). Advantageously, such antibodies are commercially available and can be used in conjunction with the cells (e.g., bound to the Fcγ receptor). Alternatively, such cells may also be commercially obtained from NantKwest as haNK cells ('high-affinity natural killer cells). Such cells may then be further genetically modified to express CXCL12 or a portion thereof, and/or to have reduced or abolished expression of CXCR4 as further discussed below.

In yet a further aspect of the inventive subject matter, the genetically engineered NK cell may also be genetically engineered to express a chimeric T-cell receptor. In especially preferred aspects, the chimeric T-cell receptor will have a scFv portion or other ectodomain with binding specificity against a tumor associated antigen, a tumor specific antigen, and a cancer neoepitope. As noted before, there are numerous manners of genetically engineering an NK cell to express such chimeric T-cell receptor, and all manners are deemed suitable for use herein. Alternatively, such cells may also be commercially obtained from NantKwest as taNK cells ('target-activated natural killer cells'). Such cells may then be further genetically modified to express CXCL12 or a portion thereof, and/or to have reduced or abolished expression of CXCR4 as further discussed below.

Where the cells are engineered to have affinity towards a cancer associated antigen or antibody with specificity towards a cancer associated antigen, it is contemplated that all known cancer associated antigens are considered appropriate for use. For example, cancer associated antigens include CEA, MUC-1, CYPB1, etc. Likewise, where the cells are engineered to have affinity towards a cancer specific antigen or antibody with specificity towards a cancer specific antigen, it is contemplated that all known cancer specific antigens are considered appropriate for use. For example, cancer specific antigens include PSA, Her-2, PSA, brachyury, etc. Where the cells are engineered to have affinity towards a cancer neoepitope or antibody with specificity towards a cancer neoepitope, it is contemplated that all known manners of identifying neoepitopes will lead to suitable targets. For example, neoepitopes may be identified from a patient tumor in a first step by whole genome analysis of a tumor biopsy (or lymph biopsy or biopsy of a metastatic site) and matched normal tissue (i.e., non-diseased tissue from the same patient) via synchronous comparison of the so obtained omics information. So identified neoepitopes can then be further filtered for a match to the patient's HLA type to increase likelihood of antigen presentation of the neoepitope. Most preferably, such matching can be done in silico.

As will be appreciated, expression of a nucleic acid molecule (CXCL12 or CXCR4) in a genetically modified NK cell can be altered relative to an unmodified NK cell in various manners. For example, alterations in gene expression include recombinant expression (e.g., where unmodified cell does not express a gene or protein at all), overexpression (e.g., up-regulation from a non-expressed or weakly expressed state), underexpression (e.g., down-regulation), and suppression of expression. In this context it should be noted that controls or standards for comparison to a sample (e.g., for determination of overexpression), include samples believed to be normal (e.g., genetically unmodified NK cells/NK92 cells) as well as laboratory values (e.g., previously obtained or from an independent reference). Thus, it should be appreciated that (over)expression or reduced or abrogated expression can be readily ascertained without undue experimentation.

With respect to reducing expression or activity of CXCR4 in NK cells, it should be noted that in some examples NK cells are obtained from a subject, and then reintroduced after manipulation (e.g., to down-regulate CXCR4), while in other examples NK cells are obtained from an allogenic subject or cell culture. Of course, it should be appreciated that the inventive subject matter is not limited to specific methods of editing gene expression or activity in a cell, but in some examples gene editing or RNA interference (RNAi) methods are used to manipulate a CXCR4 gene or other CXCR4 nucleic acid in the NK cell. For example, WO2016011381A1 described various methods of reducing expression or function of CXCR4 by RNAi mediated knockdown. Alternatively, CXCR4 expression can be abrogated by genome editing methods, including CRISPR/Cas9. In still other examples, the CXCR4 protein is targeted, for example with CXCR4 protein antagonists, such as small molecules, antibodies, or aptamers.

For example, expression and/or activity (e.g., function) of CXCR4 can be reduced in the NK cell by at least 20%, at least 30%, at least 40%, at least 50%, at least 75%, at least 80%, at least 90%, at least 95% or at least 98% as compared to expression of CXCR4 in a corresponding unmodified NK cell prior to reducing CXCR4 expression and/or activity. In some examples, reducing expression of CXCR4 includes functionally deleting one copy of a CXCR4 allele in the NK cell. In other examples, downregulation of CXCR4 or activity is done ex vivo, for example after obtaining NK cells from a donor or by contacting NK92 cells or derivatives thereof with small molecule inhibitors or antibodies.

Where CXCR4 expression is reduced via RNA interference, suitable RNAi molecules include antisense molecules, siRNAs, miRNAs, and ribozymes specific for the CXCR4 target gene, which will reduce or prevent expression of the target, for example by at least 50%, at least 60%, at least 75%, or at least 90%. In some examples, RNAi molecules are at least 12 nt in length, at least 15 nt, or at least 19 nt in length, for example, about 19 to 30 or 15 to 200 nucleotides in length, such as at least 21 nucleotides, for example at least 23 nucleotides (for example 19, 20, 21, 22, 23, 24, 25, 26, 27, 28, 29, or 30 nucleotides). Once expressed in or otherwise delivered into an NK cell, the RNAi molecule interacts with the target nucleic acid and generates an RNAi response to decrease CXCR4 expression at least 20%, at least 30%, at least 40%, at least 50%, at least 60%, at least 70%, at least 75%, at least 80%, at least 90%, at least 95%, at least 96%, at least 97%, at least 98%, or at least 99% (such as a decrease of 40% to 90%, 40% to 80% or 50% to 95%) as compared to a control (such as a unmodified NK cell with normal or wild-type CXCR4 expression). Exemplary CXCR4 RNAi molecules that target a CXCR4 sequence can be readily designed from sequences available under GenBank Accession No. NG_011587.1, AJ224869.1, NM_009911.3 or BC098322.1.

Methods of generating RNAi molecules, and introducing them into a cell, are known in the art. For example, nucleic acid molecules (such as a vector containing the RNAi molecule, or isolated/synthetic RNA) can be introduced into an NK cell by a variety of methods known to those of skill in the art, such as by transfection or transformation (e.g., by encapsulation in liposomes, by iontophoresis, by incorporation into viruses or vectors which are introduced into the cell, or by incorporation into other delivery vehicles, such as hydrogels, cyclodextrins, biodegradable nanocapsules, and bioadhesive microspheres). In some examples, RNAi molecules are expressed within an NK cell from a eukaryotic promoter. In other examples, the RNAi molecules are administered directly to a subject, for example by injection (i.v., i.p., i.m.), topical administration, oral administration, or other routes.

Where desired, expression vectors can be used to express the RNAi molecule in an NK cell. For example, an expression vector can include a nucleic acid sequence encoding at least one RNAi molecule that recognizes a target CXCR4 nucleic acid molecule. For example, the vector may contain a sequence encoding both strands of an RNAi molecule comprising a duplex. In another example, the vector may also contain a sequence encoding a single nucleic acid molecule that is self-complementary and thus forms an RNAi molecule. Suitable expression vectors are known and are, for example, described in *Nature Biotech* (2002) 19:505 and *Nature Biotech* (2002) 19: 497. In still other examples, RNAi molecules can be expressed from transcription units (see e.g., *Trends Genet* (1996) 12: 510) inserted into DNA or RNA vectors (which may be plasmids or viral vectors). RNAi expressing viral vectors can be constructed based on, for example, adeno-associated virus, retrovirus, adenovirus, lentivirus or alphavirus. In another example, pol III based constructs may be used to express RNAi molecules (see e.g., U.S. Pat. Nos. 5,902,880 and 6,146,886). The recombinant vectors capable of expressing the RNAi molecules can be delivered as described above, and persist in target cells. Alternatively, viral vectors can be used that provide for transient expression of RNAi molecules.

In further contemplated aspects, the RNAi molecule is an siRNA. siRNAs are double-stranded RNAs that can induce sequence-specific post-transcriptional gene silencing, thereby decreasing or in some examples inhibiting gene expression. In one example, siRNA triggers the specific degradation of homologous RNA molecules, such as mRNAs, within the region of sequence identity between both the siRNA and the target RNA. In some examples, siRNA molecules are about 19-27 nucleotides (nt) in length, such as 20-25 nt, or 20 to 27 nt, for example 19, 20, 21, 22, 23, 24, 25, 26 or 27 nt in length.

One of ordinary skill in the art can readily generate siRNAs which specifically bind to a target nucleic acid sequence, such as CXCR4 or any gene whose expression needs to be decreased. Commercially available kits, such as siRNA synthesizing kits from Qiagen, Origene (Rockville, Md.), Life Technologies (Grand Island, N.Y.), and SuperArray Bioscience Corporation (Hamburg, Germany) can be used to synthesize siRNA molecules. In addition, siRNAs can be obtained from commercial sources, such as from Life Technologies (Grand Island, N.Y.) and GE Dharmacon (Lafayette, Colo.). Exemplary CXCR4 siRNA molecules that target the CXCR4 sequences can be readily designed from sequences available under GenBank Accession No. NG_011587.1, AJ224869.1, NM_009911.3 or BC098322.1.

In further contemplated aspects, the RNAi molecule is an antisense oligonucleotide. Antisense RNA prevents protein translation of a target mRNA by binding to it. Thus, an antisense molecule can hybridize to a portion of the mRNA encoding CXCR4. In some examples, antisense oligonucleotides are at least 19 nucleotides (nt) in length, such as at least 20, at least 30, at least 40, at least 50, at least 75, at least 100, or at least 200 nt in length. The antisense oligonucleotide can be modified at the base moiety, sugar moiety, and/or phosphate backbone, and can include other groups such as peptides, or agents facilitating transport across a cell membrane (see e.g., *Proc. Natl Acad. Sci. USA* 1989, 86: 6553-6; Proc. Natl. Acad. Sci. USA 1987, 84: 648-52; and WO 88/09810). Of course, it should also be recognized that antisense molecules can also be synthesized by standard methods, for example by use of an automated DNA synthesizer. Exemplary CXCR4 antisense oligonucleotides that target the CXCR4 sequences can be readily designed from sequences available under GenBank Accession No. NG_011587.1, AJ224869.1, NM_009911.3 or BC098322.1.

Alternatively, the RNAi molecule may also be a ribozyme. Ribozymes are enzymatic RNA molecules capable of catalyzing the specific cleavage of RNA. Ribozymes can be synthesized and administered to the subject, or can be encoded on an expression vector, from which the ribozyme is synthesized in the targeted cell (see e.g., WO 9523225, and Nucl. Acids Res. (1995), 23: 4434-42). Methods of using ribozymes to decrease or inhibit RNA expression are known in the art. For example, specific ribozyme cleavage sites within an RNA target can be identified by scanning the target molecule for ribozyme cleavage sites that include the following sequence: GUA, GUU and GUC. Once identified, short RNA sequences of about 15 ribonucleotides (e.g., 15 to 30 or 15 to 25 ribonucleotides) corresponding to the region of the target gene containing the cleavage site may be evaluated for predicted structural features, such as secondary structure, that may render the oligonucleotide sequence unsuitable. The suitability of candidate targets can also be evaluated by testing their accessibility to hybridization with complementary oligonucleotides, using ribonuclease protection assays. An overview of ribozymes and methods of their use is provided in Kashani-Sabet (see e.g., *J. Investig. Dermatol Symp.* (2002), 7: 76-78). Methods describing endogenous and exogenous delivery are known (see e.g., Cell Mol. Neurobiol (1994)14: 523-38). For example, a plasmid that contains a sequence encoding a ribozyme directed against CXCR4, placed behind a promoter, can be transfected into the NK cells. Exemplary CXCR4 ribozymes targeting the CXCR4 sequences can be readily designed from sequences available under GenBank Accession No. NG_011587.1, AJ224869.1, NM_009911.3 or BC098322.1, and thus can include one or more sequences complementary to a CXCR4 mRNA and can include the well-known catalytic sequence responsible for mRNA cleavage (see e.g., U.S. Pat. No. 5,093,246).

Alternatively, or in addition to genetic manipulation of NK cells CXCR4 activity may also be reduced on the protein level using various CXCR4 Inhibitors. For example, CXCR4 produced in an NK cell may be contacted with one or more agents that decrease its activity, such as a decrease of at least 20%, at least 30%, at least 40%, at least 50%, at least 60%, at least 70%, at least 75%, at least 80%, at least 90%, at least 95%, at least 96%, at least 97%, at least 98%, or at least 99% (such as a decrease of 40% to 90%, 40% to 80% or 50% to 95%) as compared to a control (such as an untreated NK cell with normal or wild-type CXCR4 expression). Suitable agents acting as CXCR4 inhibitors include small molecules and specific binding agents, which competitively, allosterically, or otherwise reduce CXCL12 binding to CXCR4.

Most preferably, CXCR4 inhibitors specifically bind to the CXCR4 protein (e.g., having a sequence as listed in GenBank Accession Nos. NG_011587.1, AJ224869.1, NM_009911.3 or BC098322.1). For example, specific binding agents include CXCR4 antibodies (polyclonal or monoclonal antibodies and functional fragments thereof, as well as humanized and chimeric antibodies), CXCR4 aptamers, and other agents that bind substantially only to the CXCR4 protein.

CXCR4 antibodies can be produced using standard procedures such as those described in Harlow and Lane (Using Antibodies: A Laboratory Manual, Cold Spring Harbor Laboratory Press: Cold Spring Harbor, 1998). Antibodies can be polyclonal or monoclonal antibodies, humanized antibodies, Fab fragments, F(ab')2 fragments, single chain antibodies (scFv), or chimeric antibodies. In addition, CXCR4 antibodies are commercially available such as those from Abcam, Cambridge, Mass. (e.g., ab197203, ab181020, ab13854, or ab1670) and Novus Biologicals, Littleton, Colo. (e.g., NB100-74396, MAB170R, or NB 100-77835). In still other examples, suitable CXCR4 antibodies may also be neutralizing antibodies (e.g., obtained from a non-Hodgkin's lymphoma patient), and further known antibodies are described in U.S. Pat. No. 8,748,107.

The determination that a particular agent specifically binds to the CXCR4 protein can be made using or adapting routine procedures. For example, Western blotting can be used to determine that a given protein binding agent, such as a CXCR4 antibody or aptamer, specifically binds only to the CXCR4 protein. Other assays include competitive and non-competitive homogenous and heterogeneous enzyme-linked immunosorbent assays (ELISA) as symmetrical or asymmetrical direct or indirect detection formats, "sandwich" immunoassays, immunodiffusion assays, in situ immunoassays (for example, using colloidal gold, enzyme or radio-isotope labels), enzyme-linked immunospot assays (ELISPOT); fluorescent tests, such as used in fluorescent microscopy and flow cytometry; Western-, grid-, dot-, or tissue-blots, dip-stick assays, etc. (see e.g., Clin. Rev. Allergy Immunol (2000) 18: 341-95; Methods of Immunological Analysis, Masseyeff et al. (Eds.), VCH, New York, 1993, pp. 270-388).

In addition, various small molecule inhibitors may be employed to reduce or entirely inhibit CXCR4 activity, and there are certain small molecule inhibitors known in the art. For example, suitable inhibitors include plerixafor (AMD3100), AMD3465, T22 ([Tyr(5,12), Lys7]-polyphemusin II), T134 (des-[Cys8>13, Tyr9'12]-[d-Lys10, Pro11, 1-citrulline16]-T22 without C-terminal amide), T140 {[1-3-(2-naphthyl)alanine3]-T134}, and AMD070 (see e.g., Theranostics (2013); 3(1): 47-75). Further small molecule inhibitors include those described in US2015/0030561, and suitable nanobody peptide inhibitors of CXCR4 are described in U.S. Pat. No. 9,212,226.

Therefore, and depending on the particular manner of reducing CXCR4 activity (e.g., via genetic manipulation or small molecule inhibition) it should be appreciated that NK cells will be directly contacted with an effective amount of one or more agents that decrease CXCR4 expression and/or activity, such as one or more of the agents listed above. Most typically, the step of contacting will be performed ex vivo/in vitro before the so treated NK cells are administered to the patient. However, it is also contemplated that the NK cells may be contacted in vivo, preferably using one or more CXCR4 specific agents (e.g., small molecule inhibitors).

In further contemplated aspects, in addition to or alternatively to reduced CXCR4 expression (and regardless of the particular type of NK cell (e.g., NK92, aNK, haNK, or taNK, etc.)), it is contemplated that the NK cells are transformed or transfected with a recombinant nucleic acid construct that is suitable for (preferably inducible or temporary) expression of at least a portion of CXCL12 (e.g., full length or portion of CXCL12 that has agonistic activity and binds to the CXCR4). Suitable CXCL12 and portions thereof include full length variants, high-affinity variants and truncated variants.

With respect to (over)expression of CXCL12, it should be noted that CXCL12 polypeptides can not only repel effector T-cells while recruiting immune-suppressive regulatory T-cells to an anatomic site, but it has now been determined that CXCL12 is also capable of overcoming both acute and chronic immune destruction of transfused NK cells, and especially autologous NK92 cells. Consequently, the inventors contemplate that NK cells for administration to a patient, and especially NK92 cells and derivatives thereof (e.g., aNK cells, haNK cells, and taNK cells) may be genetically modified to express or overexpress CXCL12 when compared to the corresponding genetically unmodified cells. With respect to CXCL12 and sequences and methods related to CXCL12, it should be noted that the terms CXCL12 and SDF-1 are used interchangeably.

Nucleic acid and protein sequences for CXCL12 are well known in the art, and it should be appreciated that all known mammalian (and especially human or humanized) forms, isoforms, and splice variants are deemed suitable for use herein. For example, suitable protein sequences are described in US2016/0184234 and Nature Medicine (2000), 6: 543-8. Thus, and viewed from a different perspective, contemplated polypeptide sequences include those having at least 85%, 90%, 95%, or 100% amino acid sequence identity to the protein sequences listed below. Exemplary CXCL12 isoforms include SDF-1-alpha (Accession Number NP_954637.1), SDF-1-beta (Accession Number NP_000600.1), SDF-1-gamma (Accession Number NP_001029058), SDF-1-delta (NP_001171605.1), SDF-1-epsilon (see e.g., Yu et al. Gene (2006) vol. 374 pp. 174-9), and SDF-1-phi (see e.g., Yu et al. Gene (2006) vol. 374 pp. 174-9). Suitable nucleic acid sequences encoding CXCL12 can be obtained by reverse translation of the protein sequences, preferably using codon usage adapted to human. Alternatively, nucleic acid sequences for human CXCL12 can be obtained from NCBI as genomic sequence (NG_016861.1) and as mRNAs for various isoforms (e.g., alpha: NM_199168.3; beta: NM_000609.6; gamma: NM_001033886.2; delta: NM_001178134.1; isoform 5: NM_001277990.1). Of course, it should be appreciated that all nucleic acid sequence variations that encode the same protein sequence are also expressly contemplated herein, as well as those that encode a protein sequence having at least 85%, 90%, 95%, or 100% amino acid sequence identity to the protein sequences listed above.

Most typically, the CXCL12 is expressed from a synthetic or recombinant plasmid, a linear DNA, or RNA that is introduced into the NK cell, where the synthetic or recombinant nucleic acid may encode one or more copies of CXCL12, or different isoforms of the proteins. Likewise, additional non-CXCL12 proteins (e.g., immune stimulatory cytokine or at least one of 2B4 and CD48) may also be expressed from the same synthetic or recombinant nucleic acid. Where more than one protein is encoded, the protein may be expressed from a nucleotide sequence encoding the proteins under the control of a single promoter, or more than one promoter may be used. For example, each protein may be expressed from a separate promoter, which may be the same or different. Techniques for expression of 2 or more proteins together from the same nucleic acid are well known in the art. For example multiple transgenes can be expressed simultaneously under one promoter using P2A and T2A sequences. As noted above, it is generally preferred that the expressed CXCL12 protein will be a mammalian protein, and human and murine proteins are especially preferred. However, the native nucleotide sequences or protein sequences may also be modified, for example by one or more amino acid additions, insertions, deletions and/or substitutions, as long as the function or activity of the CXCL12 protein is not substantially or significantly altered (change in signaling activity less than 20%). Therefore, the encoded protein(s) may have an amino acid sequence which has at least 81%, 82%, 83%, 84%, 85%, 86%, 87%, 88%, 89% 90%, 91% 92% 93%, 94%, 95%, 96%, 97%, 98% or 99% sequence identity with any one of the amino acid sequences noted above. For example, activity can be measured in systems of receptor phosphorylation or calcium flux upon ligation in culture cells treated with the protein, in systems of cell chemotaxis in vitro or in vivo in models of cell recruitment to the infected protein. An example for expression of CXCL12 1α is described in WO2016/102660.

In some aspects of the inventive subject matter, an inducible promoter may be used for expression of the protein (i.e., any promoter whose function (activity, or effect in allowing or causing transcription of the coding nucleotide sequence) can be regulated or controlled). Thus, in such cases there would be no constitutive expression of the protein. Accordingly, expression of the protein may be induced, or turned on (or more particularly turned on and off). Preferably, expression may be induced, or turned on for a finite or defined time. Alternatively, promoter sequences may also be used that result in constitutive expression. Of course, where mRNA is used as the expression construct, expression will be temporary and typically not inducible.

Therefore, and among other suitable alternatives, recombinant nucleic acids will include expression vectors and linear nucleic acids (e.g., plasmids, phagemids, YAC, RNA, etc.), and it should be noted that linear nucleic acids may be integrated into the NK cell. Moreover, the recombinant nucleic acids may be suitable for transfection using conventional methods (e.g., electroporation, sonoporation, lipofection, etc.) or constructed as viral expression vector. In such case, the recombinant nucleic acid is preferably delivered to the NK cell via viral infection. For example, suitable recombinant nucleic acids include mono- and bicistronic viral vectors (e.g., a bicistronic lentiviral or adnoviral vector), linearized DNA, and RNA. Where the nucleic acid is an RNA, it is generally preferred that the RNA is prepared from in vitro transcription (IVT) of a template with specially designed primers, followed by polyA addition, to produce a construct containing 3' and 5' untranslated sequences ("UTR"), a 5' cap, and/or Internal Ribosome Entry Site (IRES), the CXCL12 encoding nucleic acid sequence. The polyA tail will typically be 50-2000 bases in length. RNA so produced can be efficiently transfected into NK cells using methods well known in the art.

In yet another aspect of the inventive subject matter, thusly modified NK cells may be used in a pharmaceutical composition, typically formulated as a sterile injectable composition with between $10^4$-$10^{11}$ cells, and more typically $10^5$-$10^9$ cells per dosage unit. However, alternative formulations are also deemed suitable for use herein, and all known routes and modes of administration are contemplated herein. As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection into the tumor, infusion, oral delivery, topical delivery, etc.).

In addition, it is contemplated that prophylactic or therapeutic administration of the NK cells may be accompanied by co-administration with immune checkpoint inhibitors to reduce possible inhibitory action on T-cells. For example, especially preferred check point inhibitors include currently available inhibitors (e.g., pembrolizumab, nivolumab, ipilimumab, etc.) under the same protocol and dosage as prescribed. Alternatively, suitable inhibitors also include those that target PD-1, CTLA-4, or other receptors that, upon ligand binding, downregulate T-cell activity. Therefore, modified NK92 cells (other NK cells, e.g., allografted or xenografted) as described herein may be employed to treat cancer, to reduce tumor cell burden in a patient having a tumor, and/or to deliver the modified NK92 cells to a tumor.

Moreover, as CXCL12 mediated processes also extend beyond immune regulation, it should be appreciated that the compositions, cells, methods presented herein may also be applicable to various alternative uses, and particularly those in which CXCL12 promotes angiogenesis and/or tissue repair through recruitment of macrophages. Consequently, modified NK92 cells (other NK cells, e.g., allografted or xenografted) as described herein may be employed to treat various conditions, and especially preferred conditions include autoimmunity and trauma (particularly to promote wound healing, etc.).

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A genetically engineered NK (natural killer) cell comprising a recombinant nucleic acid encoding at least a portion of chemokine C—X—C motif ligand 12 (CXCL12), and a transcript for downregulation of chemokine C—X—C motif receptor 4 (CXCR4), wherein the transcript for downregulation of CXCR4 is an shRNA or an siRNA.

2. The NK cell of claim 1 wherein the natural killer cell is genetically engineered to express a high-affinity Fcγ receptor or a chimeric T-cell receptor.

3. The NK cell of claim 1 wherein the cell is genetically engineered to have a reduced or abolished expression, relative to an unmodified NK cell, of at least one killer cell immunoglobulin-like receptor (KIR).

4. The NK cell of claim 3 wherein the at least a portion of CXCL12 is a full length variant of CXCL12.

5. The NK cell of claim 3 wherein the at least a portion of CXCL12 is a truncated agonist variant of CXCL12 that binds to CXCR4.

6. The NK cell of claim 1 wherein the cell has the deletion or knockout mutation for CXCR4.

7. A pharmaceutical composition comprising the genetically engineered natural killer cell according to claim 1.

8. The pharmaceutical composition of claim 7 further comprising an immune checkpoint inhibitor.

9. A genetically engineered NK cell comprising a recombinant nucleic acid encoding at least a portion of CXCL12, and wherein the NK cell is further modified to have a deletion or knockout mutation for CXCR4.

10. The NK cell of claim 9 wherein the natural killer cell is genetically engineered to express a high-affinity Fcγ receptor or a chimeric T-cell receptor.

11. The NK cell of claim 9 wherein the cell is genetically engineered to have a reduced or abolished expression, relative to an unmodified NK cell, of at least one KIR.

12. The NK cell of claim 11 wherein the at least a portion of CXCL12 is a full length variant of CXCL12.

13. The NK cell of claim 11 wherein the at least a portion of CXCL12 is a truncated agonist variant of CXCL12 that binds to CXCR4.

14. A pharmaceutical composition comprising the genetically engineered natural killer cell according to claim 5.

15. The pharmaceutical composition of claim 14 further comprising an immune checkpoint inhibitor.

* * * * *